United States Patent
Wu et al.

(10) Patent No.: US 11,959,901 B2
(45) Date of Patent: Apr. 16, 2024

(54) METHOD AND SYSTEM FOR RAPIDLY PREDICTING FOAMING TENDENCY OF EDIBLE FRYING OIL

(71) Applicant: Jiangnan University, Wuxi (CN)

(72) Inventors: Gangcheng Wu, Wuxi (CN); Hui Zhang, Wuxi (CN); Xu Li, Wuxi (CN); Xingguo Wang, Wuxi (CN); Qingzhe Jin, Wuxi (CN); Linglu Meng, Wuxi (CN); Linya Shao, Wuxi (CN); Zhengmei Zhao, Wuxi (CN); Yanting Lu, Wuxi (CN)

(73) Assignee: Jiangnan University, Wuxi (CN)

( * ) Notice: Subject to any disclaimer, the term of this patent is extended or adjusted under 35 U.S.C. 154(b) by 318 days.

(21) Appl. No.: 17/615,112

(22) PCT Filed: Apr. 14, 2020

(86) PCT No.: PCT/CN2020/084624
§ 371 (c)(1),
(2) Date: Nov. 30, 2021

(87) PCT Pub. No.: WO2020/238442
PCT Pub. Date: Dec. 3, 2020

(65) Prior Publication Data
US 2022/0229035 A1    Jul. 21, 2022

(30) Foreign Application Priority Data

May 31, 2019    (CN) .......................... 201910466001.8

(51) Int. Cl.
*G01N 33/03*    (2006.01)
*A23L 5/10*    (2016.01)
(Continued)

(52) U.S. Cl.
CPC ............... *G01N 33/03* (2013.01); *A23L 5/11* (2016.08); *B01D 46/0043* (2013.01);
(Continued)

(58) Field of Classification Search
CPC ........ G01N 33/03; G01N 27/221; A23L 5/11; B01D 46/0043; B01D 2273/30;
(Continued)

(56) References Cited

U.S. PATENT DOCUMENTS 8,486,477 B2 *   7/2013   Zeller ...................... A23F 5/40
426/564

FOREIGN PATENT DOCUMENTS

CN    107238622 A    * 10/2017
CN    107238622 A      10/2017
(Continued)

OTHER PUBLICATIONS

Shengmin Zhou et al., "Progress on Mechanism of Foaming and Influence Factors on Vegetable Oil", Grain Science and Technology and Economy, vol. 40, No. 2, Apr. 30, 2015, p. 69-72.

*Primary Examiner* — Tarun Sinha
*Assistant Examiner* — Drexel Alejandro Venero
(74) *Attorney, Agent, or Firm* — IDEA Intellectual Limited; Margaret A. Burke; Sam T. Yip

(57) ABSTRACT

Provided are method and system for rapidly predicting foaming tendency of edible frying oil, including: heating the oil; immersing a polar component content detection probe into the oil to measure an initial polar component content of the oil; at a frying state, removing the detection probe from the oil, placing frying food into the oil and frying the same taking out the frying food from the oil after frying, and measuring the largest frying oil foam height and recording the same as an initial foam height; at an air introduction state, immersing the detection probe and introducing air into (Continued)

the oil, and continuing to introduce air and heat thereinto until the polar component content in the oil is 10%; repeating the frying state; and fitting measurements and parameters into a formula.

10 Claims, 2 Drawing Sheets

(51) Int. Cl.
*B01D 46/00* (2022.01)
*B01L 3/00* (2006.01)

(52) U.S. Cl.
CPC ......... *B01L 3/5082* (2013.01); *A23V 2002/00* (2013.01); *B01D 2273/30* (2013.01); *B01L 2200/0689* (2013.01); *B01L 2300/0663* (2013.01); *B01L 2300/0681* (2013.01); *B01L 2300/1805* (2013.01)

(58) Field of Classification Search
CPC ........... B01L 3/5082; B01L 2200/0689; B01L 2300/0663; B01L 2300/0681; B01L 2300/1805; A23V 2002/00
See application file for complete search history.

(56) References Cited

FOREIGN PATENT DOCUMENTS

| | | | |
|---|---|---|---|
| CN | 107271619 A | | 10/2017 |
| CN | 206725486 U | | 12/2017 |
| CN | 108037162 A | * | 5/2018 |
| CN | 108037162 A | | 5/2018 |
| CN | 208334371 U | * | 1/2019 |
| CN | 110095515 A | | 8/2019 |
| IN | 208334371 U | | 1/2019 |
| WO | 2017002079 A1 | | 1/2017 |

\* cited by examiner

METHOD AND SYSTEM FOR RAPIDLY PREDICTING FOAMING TENDENCY OF EDIBLE FRYING OIL

CROSS REFERENCE OF RELATED APPLICATION

This application is a 35 U.S.C. 371 application of PCT application number PCT/CN2020/084624 filed Apr. 14, 2020 claiming priority from Chinese patent application number 201910466001.8 filed May 31, 2019, the disclosures of which are incorporated herein by reference.

FIELD OF THE INVENTION

The invention relates to the technical field of food processing. In particular, it relates to a method and a system for rapidly predicting foaming tendency of edible frying oil.

BACKGROUND OF THE INVENTION

As a convenient and fast cooking method, frying is widely used in food processing and catering industries. With the rapid development of the economy and the continuous improvement of household income level, China's catering industry has entered into an unprecedent golden period of development. According to the data of the National Bureau of Statistics, the turnover of the Chinese catering industry is estimated to reach 4 trillion dollars in 2017, and continues to maintain a double-digit growth. Fried food plays an important part of the catering industry, because of its attractive color, crispiness and taste, being a favorite of the majority of consumers. According to a preliminary estimate, the gross value of annual output of fried food involved in China's convenience food industry and fast food industry alone exceeds 250 billion dollars.

However, the industry has been struggling with problems of forming excessive white foam during the frying process used in food processing and catering industries. One problem is that high temperature foam may overflow the frying equipment, scald its operator and cause serious accidents. Another problem is when too much oil and foam cover the processed food, it hinders the sight of operators and seriously affects the quality control by the operators. Finally, when the foam is too great, it will lead to an excessive oil content in the fried food, which will seriously affect the quality of the processed food. Therefore, it is essential to choose a non-foaming edible oil as frying oil.

Accordingly, it is necessary to establish a rapid prediction method to comprehensively evaluate the foaming tendency of edible frying oil.

SUMMARY OF THE INVENTION

This section is intended to summarize some aspects of embodiments of the invention and to briefly introduce some preferred embodiments. In this section, as well as other parts of this application, simplifications or omissions may be made to avoid obscuring the purpose of the section, the abstract and the title, and such simplifications or omissions are not intended to limit the scope of the invention.

As one of the aspects of the present invention, the present invention overcomes the shortcomings of the prior art method in detecting foaming of edible frying oils, and provides a method for rapidly predicting foaming tendency of edible frying oils.

In order to solve the above technical problems, the present invention provides the following technical solutions: a rapid prediction of the foaming tendency of edible frying oil, which includes:

heating the edible oil, and immersing a polar component content detection probe into the oil to measure an initial polar component content in the heated edible oil;

at frying state, removing the detection probe from the edible oil, placing frying food into the edible oil and frying the same, taking out the fried food after frying, measuring the largest height of the foam of the fried oil and recording thereof as an initial foam height;

at air introduction state, immersing the detection probe into the edible oil and introducing air into the edible oil, continuing to introduce air and heat the oil until the polar component content in the oil has reached 10%;

repeating the frying state and the air introduction state, in order to obtain the polar component contents of 15%, 20%, 25% and 30%, respectively;

applying the following fitting formula: $\ln(y)=a*x+b$.

where y denotes the height of the oil foam in a unit of mm; x denotes the content of the polar component of the oil in %; a and b are fitting parameters.

taking a, b and $\exp(a*20+b)$ as indicators, quantitatively evaluating the foaming tendency of the edible frying oil, where a represents the rate of change in the height of the edible oil foam against different contents of the polar component; b represents the theoretical foaming tendency when the content of the polar component of the edible oil is 0; $\exp(a*20+b)$ indicates the foaming tendency when the polar component content of edible oil is 20% after deterioration.

In an embodiment, the edible oil is heated to 160-180° C.

In an embodiment, the air flow rate is 15-20 L/h when air is introduced into the edible oil.

In an embodiment, the mass of the edible oil is 60 g per frying.

In an embodiment, the time duration of each frying is 3 min at the frying state.

In an embodiment, the frying food has a mass of 2 g.

In an embodiment, the fitting formula fitting is further defined as:

$$a = -0.003561*SFA + 0.001682*MUFA + \\ 0.003923*PUFA - 0.004388*PUFA*P$$

$$b = 0.07454*SFA - 0.01650*MUFA - 0.06202*PUFA + \\ 0.1265*PUFA*P \exp(a*20 + b) = -0.008256*SFA + \\ 0.05379*MUFA + 0.04506*PUFA + 0.2280\ PUFA*P$$

where SFA, MUFA, PUFA and P, respectively, represent the contents of saturated fatty acids, monounsaturated fatty acids, polyunsaturated fatty acids and phospholipids in the edible oil.

As another aspect of the present invention, there is provided a system for rapidly predicting the foaming tendency of edible frying oil.

In order to solve the above technical problems, the present invention provides the following technical solutions: a rapid prediction system of the foaming tendency of edible frying oil, which includes, an air pumping unit connected to a filter unit through a first pipe to pump air into the filter unit;

the filter unit connected to anti-backflow unit through a second pipe to filter the air pumped by the air pumping unit;

the anti-backflow unit arranged between the filter unit and a frying unit to prevent the edible oil from being sucked back into the filter unit, where the anti-backflow unit is connected to a third pipe, and the end of the third pipe extends into the frying unit;

the frying unit containing the edible oil and fried food;

a heating unit arranged outside the frying unit to heat the frying unit;

a polar component detection unit detecting the polarity of the edible oil in the frying unit.

In an embodiment, the air pumping unit is an air pump; the filter unit is an air filter; the anti-backflow unit is a conical flask with a sealing piston at the opening of the flask; the frying unit is a wide-opening test tube; the heating unit is a metal bath heater; and the polar component detection unit is a polar component detector.

In an embodiment, the polar component detection unit includes a detection probe, and the detection probe extends into the frying unit to detect the polarity of the edible oil.

Beneficial effects of the invention include: the invention can predict the foaming tendency of frying oil in only 60 g in the absence of actual food frying, which saves raw materials, while showing the effect of polar components on the foaming of frying oil after oil deterioration, especially identifying the oil that does not foam when the content of polar components is low and seriously foams when the content of polar components is high, so as to enable a comprehensive evaluation of the foaming tendency. The equipment is simple and suitable for industrialization.

BRIEF DESCRIPTION OF THE DRAWINGS

In order to more clearly illustrate the technical solutions of the embodiments of the present invention, the drawings needed to be used in the description of the embodiments will be briefly introduced below. It is apparent that the drawings in the following description are only for some embodiments of the present invention. It is also apparent for those skilled in the art to obtain other embodiments based on these drawings without inventive efforts, in which.

DETAILED DESCRIPTION OF THE INVENTION

Figure 1:
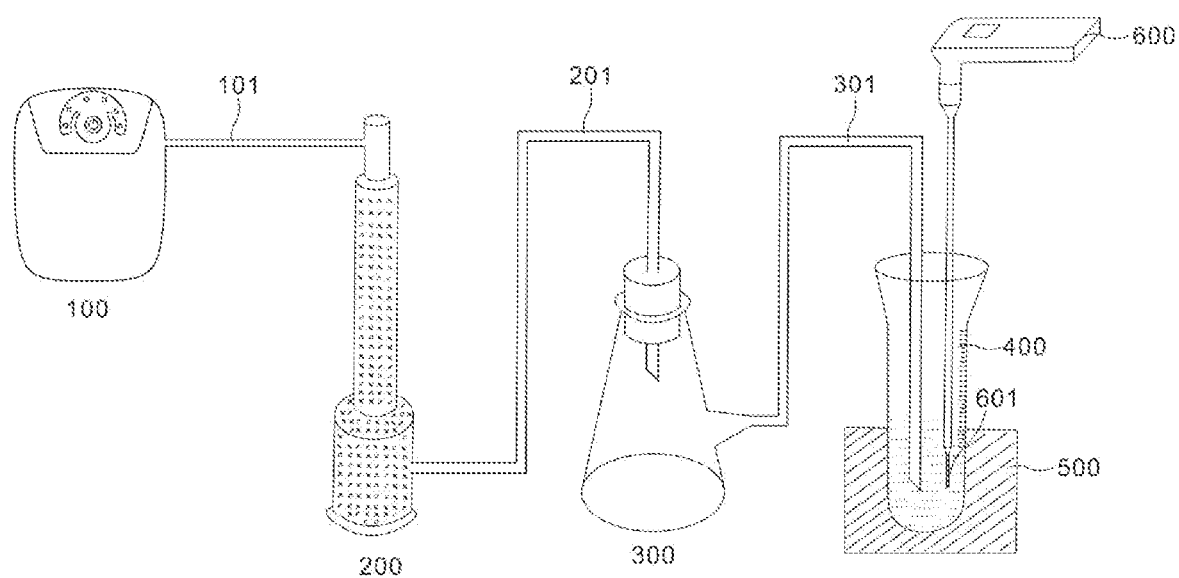
FIG. 1 is a system schematic diagram for rapid prediction of foaming tendency of edible oil at an air introduction state according to Example 3.

In order to make the aforementioned objects, features and advantages of the present invention comprehensible, embodiments accompanied with figures are described in detail below.

In the following description, numerous specific details are set forth in order to provide a thorough understanding of the present invention, but the present invention may be practiced in other ways than those specifically described and will be readily apparent to those of ordinary skill in the art without departing from the spirit of the present invention, and therefore the present invention is not limited to the specific embodiments disclosed below.

Furthermore, reference herein to "one embodiment" or "an embodiment" means that a particular feature, structure, or characteristic described in connection with the embodiment is included in at least one implementation of the invention. The use of the phrase "in one embodiment" in various parts of the present disclosure are neither necessarily all referring to the same embodiment, nor separate or alternative embodiments mutually exclusive of other embodiments.

The steps of the method for rapidly predicting the foaming tendency of frying edible oil are as follows:

(1) 60 g edible oil is heated to 160-180° C., and the polar component content detection probe is immersed into the heated oil to determine an initial polar component content (experimental equipment: a dielectric constant-based polar component detector, model Testo 270);

(2) The detection probe is removed from the heated oil; 2 g of fresh potato pieces are put into the 60 g of oil; the fried food is taken out after frying for 3 minutes; the largest height of frying oil foam is measured and recorded as an initial foam height value;

(3) At an air introduction state, the detection probe is immersed into the oil; air is introduced into the oil at a flow rate of 15-20 L/h; and the air is continuously introduced under heating until 10% of the polar component content in the oil is detected;

(4) At a frying state, the detection probe and the air venting glass tube are removed from the oil; 2 g of fresh potato pieces are put into the 60 g of oil; after frying for 3 minutes, the fried food is taken out from the oil; the largest height of the frying oil foam is measured and recorded;

(5) At the air introduction state, the detection probe is immersed into the oil; air is introduced into the oil at a flow rate of 15-20 L/h; and the air is continuously introduced under heating until 15% of the polar component content in the oil is detected;

(6) At the frying state, the detection probe and the air venting glass tube are removed from the oil; 2 g of fresh potato pieces are put into the 60 g of oil; after frying for 3 minutes, the fried food is taken out from the oil; the largest height of the frying oil form is measured and recorded;

(7) At the air introduction state, the detection probe is immersed into the oil; air is introduced into the oil at a flow rate of 15-20 L/h; and the air is continuously introduced under heating until a 20% of the polar component content in the oil is detected;

(8) At the frying state, the detection probe and an air venting glass tube are removed from the oil; 2 g of fresh potato pieces are put into the 60 g of oil; after frying for 3 minutes, the fried food is taken out from the oil; the largest height of the frying oil form is measured and recorded;

(9) At the air introduction state, the detection probe is immersed into the oil; air is introduced into the oil at a flow rate of 15-20 L/h; the air is continuously introduced under heating until a 25% of the polar component content in the oil is detected;

(10) At the frying state, the detection probe and an air venting glass tube are removed from the oil; 2 g of fresh potato pieces are put into the 60 g of oil; after frying for 3 minutes, the fried food is taken out from the oil; the largest height of the frying oil foam is measured and recorded;

(11) At the air introduction state, immerse the detection probe into the oil, and inject air into the oil at a flow rate of 15-20 L/h, and keep introducing air and heating until a 30% of the polar component content of the oil is detected;

(12) At the frying state, the detection probe and an air venting glass tube are removed from the oil; 2 g of fresh potato pieces are put into the 60 g of oil; after frying for 3 minutes, the fried food is taken out from the oil; the largest height of the frying oil foam is measured and recorded;

(13) Fitting into the following Formula: $\ln(y)=a*x+b$, where y denotes the height of the oil foam in a unit of mm; x denotes the content of the polar component in the oil in a unit of %; a and b are fitting parameters.

Taking experimental results to obtain a, b and exp (a*20+b) as indicators, frying foaming tendency of edible oil is quantitatively evaluated, where a represents the rate of change of the edible oil foam height with the content of the polar component; b represents the theoretical foaming tendency when the content of the polar component of the edible oil is 0, exp (a*20+b) indicates the foaming tendency when the polar component content of edible oil is 20% after deterioration.

The greater the absolute value of a, the faster is the rate of change of the oil foam height against different contents of polar components; the greater the value of b, the greater the foaming tendency of non-fried oil; the greater the value of exp (a*20+b), the greater the foaming tendency of fried oil after deterioration.

The detection probe for measuring the content of polar components in the oil shall adjust the detection results based on the "GB 5009.202-2016 National Food Safety Standard Determination of Polar Components (PC) in Edible Oils".

EXAMPLES

Example 1

Oil samples: soybean oil, rapeseed oil, sunflower seed oil and cottonseed oil are purchased in local supermarkets.

The rapid prediction device for frying foaming tendency of edible oil is used to process samples in steps. The specific steps are as follows:

(1) 60 g edible oil is heated to 180° C., and the polar component content detection probe is immersed into the heated oil to determine an initial polar component content;

(2) At a frying state, the detection probe is removed from the heated oil; 2 g of fresh potato pieces are put into the 60 g of oil; the fried food is taken out after frying for 3 minutes; the largest height of frying oil foam is measured and recorded as an initial foam height value;

(3) At an air introduction state, the detection probe is immersed into the oil; air is introduced into the oil at a flow rate of 20 L/h; and the air is continuously introduced under heating until 10% of the polar component content in the oil is detected;

(4) At a frying state, the detection probe and the air venting glass tube are removed from the oil; 2 g of fresh potato pieces are put into the 60 g of oil; after frying for 3 minutes, the fried food is taken out from the oil; the largest height of the frying oil foam is measured and recorded;

(5) At the air introduction state, the detection probe is immersed into the oil; air is introduced into the oil at a flow rate of 20 L/h; and the air is continuously introduced under heating until 15% of the polar component content in the oil is detected;

(6) At the frying state, the detection probe and the air venting glass tube are removed from the oil; 2 g of fresh potato pieces are put into the 60 g of oil; after frying for 3 minutes, the fried food is taken out from the oil; the largest height of the frying oil form is measured and recorded;

(7) At the air introduction state, the detection probe is immersed into the oil; air is introduced into the oil at a flow rate of 20 L/h; and the air is continuously introduced under heating until a 20% of the polar component content in the oil is detected;

(8) At the frying state, the detection probe and an air venting glass tube are removed from the oil; 2 g of fresh potato pieces are put into the 60 g of oil; after frying for 3 minutes, the fried food is taken out from the oil; the largest height of the frying oil form is measured and recorded;

(9) At the air introduction state, the detection probe is immersed into the oil; air is introduced into the oil at a flow rate of 20 L/h; the air is continuously introduced under heating until a 25% of the polar component content in the oil is detected;

(10) At the frying state, the detection probe and an air venting glass tube are removed from the oil; 2 g of fresh potato pieces are put into the 60 g of oil; after frying for 3 minutes, the fried food is taken out from the oil; the largest height of the frying oil foam is measured and recorded;

(11) At the air introduction state, immerse the detection probe into the oil, and inject air into the oil at a flow rate of 20 L/h, and keep introducing air and heating until a 30% of the polar component content of the oil is detected;

(12) At the frying state, the detection probe and an air venting glass tube are removed from the oil; 2 g of fresh potato pieces are put into the 60 g of oil; after frying for 3 minutes, the fried food is taken out from the oil; the largest height of the frying oil foam is measured and recorded;

(13) Fitting into the following Formula: $\ln(y)=a*x+b$, where y denotes the height of the oil foam in a unit of mm; x denotes the content of the polar component in the oil in a unit of %; a and b are fitting parameters.

Taking experimental results to obtain a, b and exp (a*20+b) as indicators, frying foaming tendency of edible oil is quantitatively evaluated, where a represents the rate of change of the edible oil foam height with the content of the polar component; b represents the theoretical foaming tendency when the content of the polar component of the edible oil is 0, exp (a*20+b) indicates the foaming tendency when the polar component content of edible oil is 20% after deterioration.

Example 2

The method of Example 1 was used to determine the samples of soybean oil, rapeseed oil, sunflower oil, and cottonseed oil. The polar components increased gradually with the time of frying, and the largest foam height of the polar components are shown in Table 1.

TABLE 1

Determination of the largest foam height corresponding to the
content of each polar component of the four oil samples:

| Soybean oil | | Rapeseed oil | | Sunflower oil | | Cottonseed oil | |
|---|---|---|---|---|---|---|---|
| Polar component (%) | Largest foam height (mm) | Polar component (%) | Largest foam height (mm) | Polar component (%) | Largest foam height (mm) | Polar component (%) | Largest foam height (mm) |
| 2.2 | 0.3 | 1.7 | 0.1 | 1.4 | 0.2 | 3.1 | 0.4 |
| 10 | 1.8 | 10 | 1.4 | 10 | 1.7 | 10 | 1.2 |
| 15 | 4.3 | 15 | 4.2 | 15 | 3.8 | 15 | 2.8 |
| 20 | 10.7 | 20 | 8.5 | 20 | 6.8 | 20 | 4.8 |
| 25 | 13.1 | 25 | 10.8 | 25 | 8.7 | 25 | 8.8 |
| 30 | 19.5 | 30 | 16.2 | 30 | 11.5 | 30 | 14.4 |

It can be seen from Table 1 that as the content of the polar components of the oil increases, the maximum height of the foam increases. Moreover, the studies in the present invention provide that the initial largest foam height between different oils are different. The level of increase in the value of the largest foam height is also different among different levels of increase in the content of the polar components of the oil. Therefore, the present invention provides a method that can comprehensively and reasonably reflect the foaming properties of oils. The results from fitting the data into the evaluation formula $\ln(y)=a*x+b$ to demonstrate the foaming properties of oils of the present invention are shown in Table 2.

TABLE 2

The fitting results from the formula $\ln(y) = a*x + b$:

| | Soybean oil | Rapeseed oil | Sunflower oil | Cottonseed oil |
|---|---|---|---|---|
| Initial foam height value | 0.3 | 0.1 | 0.2 | 0.4 |
| a | 0.1494 | 0.1739 | 0.1373 | 0.1331 |
| b | −1.0897 | −1.8186 | −1.200 | −1.1692 |
| exp(a*20 + b) | 6.6745 | 5.2562 | 4.6926 | 4.4495 |

Chemical significance of three parameters a, b and exp(a*20+b) is obtained by fitting into the formula in combination with the detection system. The results are as follows:

$$a = -0.003561*SPA + 0.001682*MUFA + 0.003923*PUFA - 0.004388*PUFA*P$$

$$b = 0.07454*SFA - 0.01650*MUFA - 0.06202*PUFA + 0.1265*PUFA*P$$

In the formula:

$$\exp(a*20 + b) = 0.008256*SFA + 0.05379*MUFA + 0.04506*PUFA + 0.2280\ PUFA*P,$$

SFA, MUFA, PUFA and P represent the contents of saturated fatty acids, monounsaturated fatty acids, polyunsaturated fatty acids and phospholipids, respectively, in edible oil. The oil foaming characteristics of the parameters a, b and exp(a*20+b) are the result of the combined effect of fatty acid composition and phospholipid content. The results of the examples align with the characterization descriptions in some of the reports. This solution further realizes the characterization descriptions of oil foaming characteristics by taking the steps described herein.

It can be seen from the above results that when the content of the polar components of the oil increases, the largest height of the foam increases. At the same time, after a long-term frying, an initial foam height of the detected oils is not completely correlated with the foaming performance at the later stage of frying. For example, the initial foam height of sunflower oil is lower than that of cottonseed oil. However, with an increase in the content of the polar components in the oil, the foam height of the deteriorated sunflower oil is higher than that of the deteriorated cottonseed oil. Therefore, the foam height of non-fried edible oil cannot correspond to the foaming property of deteriorated oil. Therefore, the invention includes an evaluation method for the initial foam height, the rate of change in foam height, and the foam height of the oil after deterioration, so as to comprehensively and reasonably evaluate the foaming performance of frying oil. In the prior art, it is too biased to calibrate the foaming property of oil only by the initial foam height.

Another advantage of the present invention is that the a value obtained by fitting the data/results into the Formula represents the rate of change in the height of the oil foam against different contents of the polar component. This indicator is not only related to the rate of increase in the foam height, but also closely related to the rate of quality deterioration of oil during the frying process. At the same time, it can be used to evaluate the stability of oil during the frying process, and also act as an essential element to ensure the food safety of frying oil and fried food. According to the studies in the present invention, the residence time of the polar component content of 20% in the frying process is the longest; exp (a*20+b) represents the foaming tendency when the polar component content of the oil is 20% after deterioration. Taking exp(a*20+b) as the foaming tendency value of edible oil to be tested is more reasonable than using only the initial foam height value to calibrate the foaming properties of oil.

The present invention can predict the frying foaming tendency of oil with as low as 60 g sample in the absence of actual food frying, which saves raw materials, shows the influence of polar components on the foaming of frying oil after oil deterioration, especially identifying the oil that does not foam when the content of polar components is low and seriously foam when the content of polar components is high, so as to enable a comprehensive evaluation of foaming performance. The equipment is simple and suitable for industrialization.

Example 3

Figure 2:
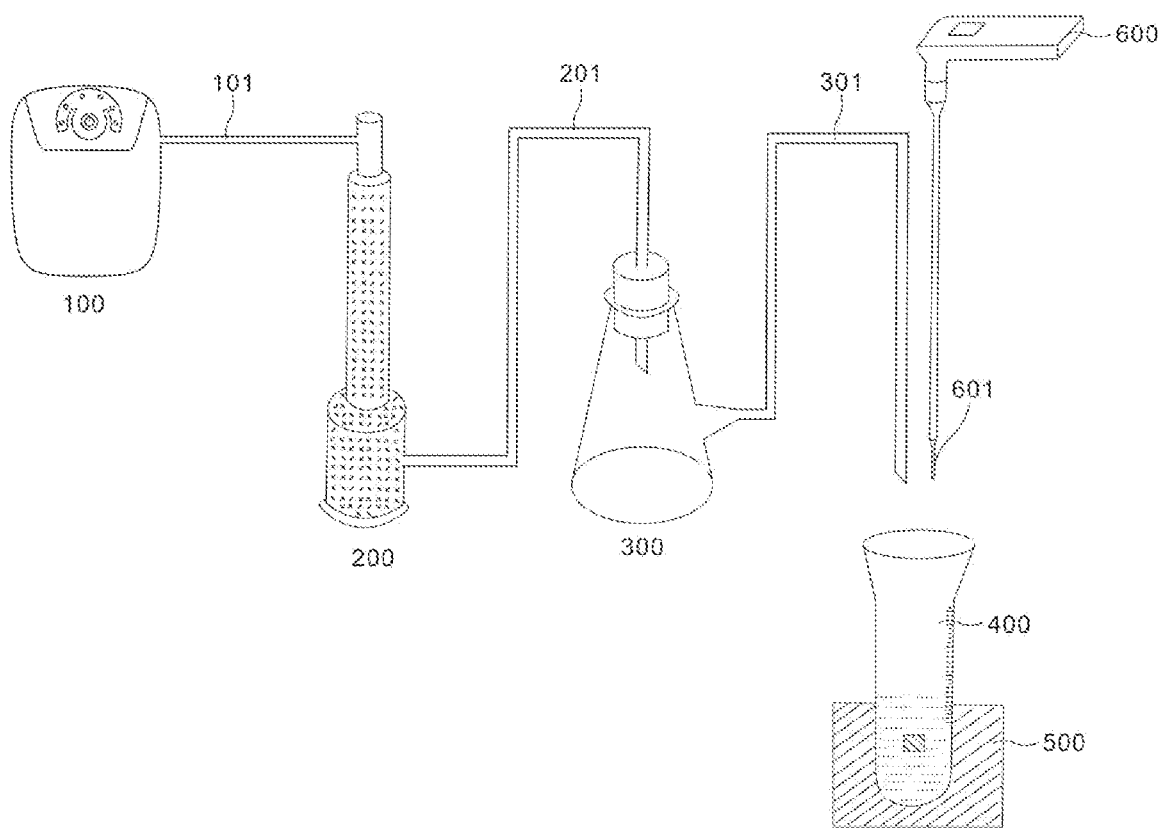
FIG. 2 is a system schematic diagram for rapid prediction of foaming tendency of edible oil at a frying state according to Example 3.

System for rapidly predicting foaming tendency of edible frying oil:

As shown in FIG. 1 and FIG. 2, the rapid prediction system for foaming tendency of frying edible oil includes an air pumping unit 100, a filter unit 200, an anti-backflow unit 300, a frying unit 400, a heating unit 500 and a polar component detection unit 600.

Specifically, the air pumping unit 100 is used to pump the air continuously into the frying unit 400 at an air introduction state. The air pumping unit 100 is connected to a filter unit 200 through a first pipe 101 to pump air into the filter unit 200. The filter unit 200 is used to filter the air. The filter unit 200 is connected to the anti-backflow unit 300 through a second pipe 201, the end of the second pipe 201 extends into the anti-backflow unit 300. The anti-backflow unit 300 is used to prevent the frying oil in the frying unit 400 from being sucked back into the filter unit 200 due to negative pressure. When a negative pressure is generated in the frying unit 400, the frying oil in the frying unit 400 flows into the anti-backflow unit 300 through the third pipe 301. The anti-backflow unit 300 is connected to the third pipe 301, and the end of the third pipe 301 extends into the frying unit 400. The frying unit 400 has a scale for measuring the foam height of frying oil. The end of the polar component detection unit 600 is a detection probe 601. The detection probe 601 extends into the frying unit 400 to detect the content of polar components in the frying oil. The heating unit 500 is arranged outside the frying unit 400 and is used for heating the frying oil in the frying unit 400. When measuring the content of the polar components of the frying oil in the air introduction detection state, the third pipe 301 and the detection probe 601 extend into the frying unit 400 at the same time. The third pipe 301 passes the air pumped by the air pumping unit 100 into the frying unit 400 through the filter unit 200 and the anti-backflow unit 300, and the detection probe 601 detects the content of polar components. In the frying state, the third pipe 301 and the detection probe 601 are moved out of the frying unit 400, and the frying unit 400 is filled with frying oil and fried objects. The heating unit 500 heats and fries the frying unit 400, and reads the foam height value through the scale on the side wall of the frying unit 400.

The working process of the system for rapidly predicting the frying foaming tendency of edible oil of the invention is as follows: in the frying state (as shown in FIG. 2), the frying unit 400 contains frying oil and frying objects. The heating unit 500 heats and fries the frying unit 400, and reads the foam height value through the scale on the side wall of the frying unit 400. When the polar component content of the frying oil is measured at the air introduction state (as shown in FIG. 1), the air pumping unit 100 pumps the air into the filter unit 200 through the first pipe 101, and the filtered air enters the anti-backflow unit 300 through the second pipe 201. After the air is passed through the third pipe 301 into the frying oil in the frying unit 400, the detection probe 601 of the polar component detection unit 600 extends into the frying oil for detecting the content of the polar component.

Further, the air pumping unit 100 is an air pump; the filter unit 200 is an air filter for filtering impurities in the air; the anti-backflow unit 300 is a conical flask with a sealed piston at the opening of the flask. The second pipe 201 extends through the sealed piston into the conical flask from top to bottom, so that when a negative pressure is generated in the frying unit 400, the frying oil in the frying unit 400 flows into the anti-backflow conical flask through the third pipe 301. The frying unit 400 can be a wide-opening test tube, preferably a round bottom test tube, and the side wall of the test tube is provided with a scale for measuring the foam height of the frying oil. The heating unit 500 may be a metal bath heater, and the polar component detection unit 600 is a polar component detector, preferably a polar component detector based on dielectric constant, which gives the result of polar component content in the oil by measuring its dielectric constant.

The detection probe 601 adjusts the detection results based on "GB 5009.202-2016 National Food Safety Standard Determination of Polar Component (PC) in Edible Oils".

It should be noted that the above-mentioned embodiments are only for illustrating the technical solutions of the present invention but not for limiting. Although the present invention has been described in detail with reference to the preferred embodiments, it should be understood by those skilled in the art that modifications or equivalent substitutions may be made on the technical solutions of the present invention without departing from the spirit and scope of the technical solutions of the present invention, which should be covered by the appended claims of the present invention.

What we claim:

1. A method for rapidly predicting foaming tendency of edible frying oil, comprising:

heating the oil, and immersing a polar component content detection probe into the oil to measure an initial polar component content of the oil;

at a frying state, removing the detection probe from the oil, placing food into the oil and frying thereof, taking out the food from the oil after frying, measuring a largest oil foam height and recording thereof as an initial foam height;

at an air introduction state, immersing the detection probe into the oil and introducing air into the oil, continuing to introduce air and heat thereinto until 10% of polar component is detected in the oil;

repeating the frying state and the air introduction state to obtain the largest height of the oil foam until the polar component content reaches 15%, 20%, 25% and 30%, respectively;

fitting the measured foam height into the following formula:

$$\ln(y) = a*x + b,$$

wherein y denotes the height of the oil foam in a unit of mm; x denotes the content of the polar component of the oil in a unit of %; a and b are fitting parameters;

taking a, b and exp (a*20+b) as indicators, quantitatively evaluating a foaming tendency of the oil, wherein a represents the rate of change in the oil foam height against different contents of the polar component, and b represents a theoretical foaming tendency when the content of the polar component of the oil is 0, exp (a*20+b) indicates the foaming tendency when the polar component content in the oil is 20% after deterioration.

2. The method for rapidly predicting foaming tendency of edible frying oil of claim 1, wherein the heating of the oil is at 160 to 180° C.

3. The method for rapidly predicting foaming tendency of edible frying oil of claim 1, wherein the introducing of the air into the oil is at an air flow rate of 15-20 L/h.

4. The method for rapidly predicting foaming tendency of edible frying oil of claim 1, wherein the mass of oil is 60 g per frying.

5. The method for rapidly predicting foaming tendency of edible frying oil of claim 1, wherein at the frying state, each frying last for 3 minutes.

6. The method for rapidly predicting foaming tendency of edible frying oil of claim 1, wherein the food has a mass of 2 g.

7. The method for rapidly predicting foaming tendency of edible frying oil of claim 1, wherein the indicators are further represented by, $$a = -0.003561 * SFA + 0.001682 * MUFA +$$
$$0.003923 * PUFA - 0.004388 * PUFA * P;$$
$$b = 0.07454 * SFA - 0.01650 * MUFA -$$
$$0.06202 * PUFA + 0.1265 * PUFA * P;$$
$$\exp(a*20 + b) = -0.008256 * SFA + 0.05379 * MUFA +$$
$$0.04506 * PUFA + 0.2280\ PUFA * P;$$

wherein SFA, MUFA, PUFA and P represent contents of saturated fatty acids, monounsaturated fatty acids, polyunsaturated fatty acids and phospholipids, respectively, in the oil.

8. A system for rapidly predicting foaming tendency of edible frying oil according to the method of any one of claim 1, comprising: an air pumping unit connected to a filter unit through a first pipe to pump air into the filter unit; the filter unit connected to an anti-backflow unit through a second pipe to filter the air pumped by the air pumping unit; the anti-backflow unit arranged between the filter unit and a frying unit to prevent the edible oil from being sucked back into the filter unit, the anti-backflow unit connected to a third pipe, and one end of the third pipe extending into the frying unit; the frying unit for containing edible oil and fried food; a heating unit arranged outside the frying unit to heat the frying unit; a polar component detection unit detecting the polarity of the edible oil in the frying unit.

9. The system for rapidly predicting foaming tendency of edible frying oil of claim 8, wherein: the air pumping unit is an air pump; the filter unit is an air filter; the anti-backflow unit is a conical flask with a scaling piston at the flask mouth, the frying unit is a wide mouth test tube, the heating unit is a metal bath heater, and the polar component detection unit is a polar component detector.

10. The system for rapidly predicting foaming tendency of edible frying oil of claim 9, wherein the polar component detection unit comprises a detection probe, and wherein the detection probe extends into the frying unit to detect the polarity of the edible oil.

* * * * *